(12) United States Patent
Houwen et al.

(10) Patent No.: US 6,911,313 B2
(45) Date of Patent: Jun. 28, 2005

(54) PROCESS FOR DISCRIMINATING AND COUNTING ERYTHROBLASTS

(75) Inventors: Berend Houwen, Redlands, CA (US); Fu-sheng Wang, Claremont, CA (US); Tomohiro Tsuji, Hyogo (JP); Takashi Sakata, Hyogo (JP); Yukio Hamaguchi, Hyogo (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/058,323

(22) Filed: Apr. 9, 1998

(65) Prior Publication Data

US 2002/0006631 A1 Jan. 17, 2002

Related U.S. Application Data (63) Continuation-in-part of application No. 09/019,932, filed on Feb. 6, 1998, now abandoned.

(51) Int. Cl.[7] .......................... G01N 33/53; G01N 21/76
(52) U.S. Cl. .................. 435/7.2; 436/17; 436/18; 436/56; 436/63; 436/164; 436/172; 436/175; 436/176; 436/177; 435/2; 435/6; 435/7.21; 435/7.24; 435/7.25
(58) Field of Search .................... 433/10, 17, 18, 433/43, 56, 63, 74, 164, 172, 174, 175, 501, 503, 519, 536, 176, 177; 435/2, 4, 6, 7, 29, 34, 39, 91.2, 7.21, 7.24, 7.25; 422/63, 67, 73, 82.08; 250/461.2; 436/10, 17, 63, 43, 74, 164, 172, 174, 175, 501, 503, 579, 536

(56) References Cited

U.S. PATENT DOCUMENTS

| | | | | |
|---|---|---|---|---|
| 5,047,321 A | * | 9/1991 | Loken et al. | 435/6 |
| 5,057,413 A | * | 10/1991 | Terstappen et al. | 435/6 |
| 5,188,935 A | * | 2/1993 | Leif et al. | 435/7.24 |
| 5,298,426 A | * | 3/1994 | Inami et al. | 436/63 |
| 5,496,734 A | * | 3/1996 | Sakata | 436/63 |
| 5,559,037 A | | 9/1996 | Kim et al. | |
| 5,641,628 A | * | 6/1997 | Bianchi | 435/6 |
| 5,648,225 A | * | 7/1997 | Kim et al. | 435/7.24 |
| 5,879,900 A | * | 3/1999 | Kim et al. | 435/7.24 |
| 5,939,326 A | * | 8/1999 | Chupp et al. | 436/43 |

FOREIGN PATENT DOCUMENTS

| | | |
|---|---|---|
| JP | Hei 2 (1990)-73157 | 3/1990 |
| JP | Hei 4 (1992)-268453 | 9/1992 |
| JP | Hei 5 (1993)-34251 | 9/1993 |
| JP | Hei 8(1996) - 1434 | 1/1996 |
| JP | 2620810 | 4/1997 |
| WO | Hei 8 (1996)-507147 | 7/1996 |

OTHER PUBLICATIONS

Lehninger, Albert L., Principles of Biochemistry, (1982), p. 55.*

* cited by examiner

Primary Examiner—Long V. Le
Assistant Examiner—Gailene R. Gabel
(74) Attorney, Agent, or Firm—Bryan Cave LLP (57) ABSTRACT

A method for discriminating and counting erythroblasts comprises the steps of: (i) staining leukocytes in a hematologic sample by adding a fluorescent labeled antibody capable of binding specifically with leukocytes to the hematologic sample; (ii) raising the permeability only of cell membranes of erythroblasts in the hematologic sample to a nucleotide fluorescent dye which does not permeate a cell membrane usually, the nucleotide fluorescent dye having a fluorescent spectrum capable of being distinguished from that of a fluorescent labeling compound of the fluorescent labeled antibody in step (i); (iii) staining nuclei of the erythroblasts in the hematologic sample with the nucleotide fluorescent dye; (iv) subjecting the hematologic sample to flowcytometry to detect at least two fluorescent signals from each cell; and (v) discriminating and counting the erythroblasts from difference in intensity between the at least two fluorescent signals.

13 Claims, 7 Drawing Sheets

Intensity of Red Fluorescence

FIG. 4B

Intensity of Red Fluorescence

FIG. 4C

Intensity of Red Fluorescence

Ly : LYMPHOCYTE
Mo : MONOCYTE
Gran : GRANULOCYTE
WBC : TOTAL LEUKOCYTE
Gho : GHOST
NRBC : ERYTHROBLAST

PROCESS FOR DISCRIMINATING AND COUNTING ERYTHROBLASTS

CROSS REFERENCE TO RELATED APPLICATION

This application is a continuation-in-part of U.S. Ser. No. 09/019,932 filed on Feb. 6, 1998 now abandoned.

BACKGROUND OF THE INVENTION

1. Field of the Invention

The present invention relates to a method for discriminating and counting erythroblasts. In particular, the present invention relates to a method for accurately discriminating and counting erythroblasts by flowcytometry.

2. Description of the Prior Art

The discrimination and counting of erythroblasts are of great use in a field of clinical examination since it provides very useful information for the diagnosis of diseases and prognosis of diseases.

Erythroblasts, which are also called nucleated red blood cells, are normally contained in the bone marrow, but not in peripheral blood except newborns. The appearance of erythroblasts in peripheral blood indicates a possible presence of a disease, such as leukemias, hemolytic anemia, iron deficiency anemia or pernicious anemia, and other non-hematologic/oncologic disorders. Thus the discrimination and counting of erythroblasts are very effective for the diagnosis of any such disease and for the prognosis in some of them.

Conventionally, it has been usual to prepare a smear of blood, add an appropriate dye to the smear of blood and examine it by a microscope for discriminating and counting erythroblasts. However, such a method requires not only time-consuming, complicated pretreatment of blood for examination but also considerable expertise and skills for obtaining accurate results.

Recently, there have been available a variety of apparatuses for the fully automated discrimination and counting of leukocytes based on the principle of a flowcytometer, and there have been proposed a number of methods for analyzing blood contents using such apparatuses.

For example, Japanese Unexamined Patent Publication No. HEI 4(1992)-268453 discloses a method for discriminating and counting erythroblasts in a blood sample. This method includes the treatment of the blood sample with an acid reagent fluid of hypotonic osmolarity, the staining of nuclei of erythroblasts with a fluorescent dye solution and the detection of scattered light and fluorescent light by a flowcytometer.

Japanese Unexamined Patent Publication No. HEI 5(1993)-34251 discloses a method of determining erythroblasts. This method includes the treatment of a blood sample with an acid reagent fluid of hypotonic osmolarity, the staining of the blood sample with four kinds of dyes including Astrazon Yellow 3G and Neutral Red which are fluorescent dyes and the detection of red fluorescent light and green fluorescent light by a flowcytometer.

Published Japanese translation of PCT international publication for patent application No. HEI 8(1996)-507147 discloses a method for determining nucleated red blood cells by detecting forward scattered light or fluorescence-side scattered light by a flowcytometer using a specific amount of a non-quaternary ammonium salt, an aliphatic aldehyde, a non-phosphate buffer, a reagent having a specific pH and a specific osmolarity and a nuclear dye such as ethidium homodimer.

U.S. Pat. No. 5,559,037 discloses a method for counting erythroblasts. This method includes the lysis of erythrocytes and cell membranes of erythroblasts, the staining with a vital nuclear dye capable of staining erythroblasts but not leukocytes and the detection of scattered light at two different angles and fluorescent light by a flowcytometer.

In these methods, however, cell membranes of leukocytes as well as erythroblasts become easily damaged especially in a hematologic sample with increasing time after collection of blood. Accordingly, some leukocytes are stained with the dye that on purpose to stain erythroblasts. As a result, erythroblasts cannot be accurately determined. For example, in the case where scattered light and fluorescent light are detected, a site where erythroblasts appear overlaps or overlays a site where leukocytes appear. Especially, when lymphoid cells are damaged, it becomes more difficult to distinguish erythroblasts from damaged lymphoid cells clearly and thus the presence of erythroblasts cannot be detected accurately.

Moreover, in recent years, more and more medical laboratories send blood samples taken from patients to institutions specialized for mass examination in order to reduce costs and improve efficiency. In such a case, it sometimes takes one day or more from the collection of blood to the examination.

Besides, it is difficult to accurately discriminate and count erythroblasts in a sample containing lymphoblasts or a sample in which chemotherapy or the like has made membranes of leukocytic cells ready to be damaged by an hemolytic agent, even if the sample does not go through change with time.

Additionally, Japanese Patent Publication No. HEI 8(1996)-1434 discloses a method for identifying nucleated red blood cells and the like. This method includes the addition of thiazole orange to a blood sample, the addition of two kinds of fluorescent labeled antibodies, anti-CD45 and anti-CD71, and the detection of signals at at least three fluorescent channels and at least two light scattering channels by a flowcytometer.

This method uses two antibodies and one fluorescent dye as reagents and has a disadvantage in that the reagents are expensive. Since the method can examine immature, nucleated red blood cells only with the combination of these specific antibodies with the specific dye, it is impossible to analyze erythroblasts cheaply by use of this method.

Further, Japanese Unexamined Patent Publication No. HEI 2(1990)-73157 discloses a method for analyzing various kinds of cells including nucleated red blood cells by detecting signals at least three fluorescent channels and at least two light scattering channels by a flowcytometer using two kinds of fluorescent nucleic acid dyes and a fluorescent monoclonal antibody.

According to this method, in order to discriminate erythroblasts from leukocytes, a blood sample is stained with the fluorescent monoclonal antibody, and side scattered light is measured. However, since this publication lacks description about the distinction of erythroblasts from platelets and debris, it is difficult to count erythroblasts exactly by this method.

Japanese Patent No. 2620810 discloses a method for detecting fluorescent light and scattered light by a flowcytometer. The method includes the lysis of erythrocytes and the addition of a monoclonal antibody, a fixative and a nucleic acid dye which binds with DNA first.

According to this method, since a sample must be first subjected to erythrolytic treatment, the sample must be subjected to centrifugal cleaning immediately after the erythrolytic treatment. Thus absolute counting is difficult. Moreover, since this centrifugal cleaning involves complicated operation, results of detection vary significantly depending on the skill of an examiner.

Under these circumstances, there has been a demand for an easy, inexpensive method for analyzing erythroblasts accurately even in a hematologic sample collected some time before. There has also been a demand for a method for classifying and counting erythroblasts according to a degree of maturity thereof. However, such method has not been established so far.

SUMMARY OF THE INVENTION

The present invention provides a method for discriminating and counting and staging erythroblasts comprising the steps of:

(i) staining leukocytes in a hematologic sample by adding a fluorescent labeled antibody capable of binding specifically with leukocytes to the hematologic sample;

(ii) raising the permeability only of cell membranes of erythroblasts in the hematologic sample to a nucleotide fluorescent dye which does not permeate a cell membrane usually;

(iii) staining nuclei of the erythroblasts in the hematologic sample with the nucleotide fluorescent dye;

(iv) subjecting the hematologic sample to flowcytometry to detect at least two fluorescent signals from each cell; and (v) discriminating and counting the erythroblasts from difference in intensity between the at least two fluorescent signals.

The present invention is now described in detail by way of embodiments, which are not intended to limit the scope of the invention, with reference to the accompanying drawings in which:

DETAILED DESCRIPTION OF THE INVENTION

The hematologic sample used in step (i) according to the present invention is a sample of body fluid containing leukocytes and erythroblasts, such as a sample of peripheral blood, bonemarrow or lymphoid tissue or urine, or a sample taken by apheresis.

Fluorescent labeled antibodies capable of binding specifically with leukocytes such as anti-CD45 antibody. A commercially available antibody product may be employed.

Fluorescent labeling compounds for converting the above-mentioned antibodies to the fluorescent labeled antibodies include phycoerythrin, fluorescein isothiocyanate (FITC), allophycocyanin, Texas Red, CY5, and a peridinin chlorophyll complex, which may be used singly or as a combination thereof. Preferably, these fluorescent labeling compounds have a fluorescent spectrum different from that of the fluorescent dye specific to nucleotide explained later. Phycoerythrin and fluorescein isothiocyanate are preferred among the above compounds.

The mixture ratio of the hematologic sample to the fluorescent labeled antibody may suitably be changed depending on the state of the hematologic sample, the kind of the fluorescent labeled antibody and the like, but the mixture ratio may be about 10:1 to 2:1 by volume, for example. The mixing of the hematologic sample with the fluorescent labeled antibody may be carried out for a time period suitably set depending on temperature, but preferably at room temperature for 15 to 30 minutes or in an ice bath for 30 to 45 minutes, for example.

In step (ii) of the present invention, the permeability only of cell membranes of erythroblasts to the nucleotide fluorescent dye is raised. Usually, the nucleotide fluorescent dye does not penetrate cell membranes.

Examples of the nucleotide fluorescent dyes are propidium iodide, N-methyl-4-(1-pyrene)vinyl-propidium iodide, ethidium bromide, TOTO-1, TOTO-3, YOYO-1, YOYO-3, BOBO-1, BOBO-3, ethidium homodimer-1 (EthD-1), ethidium homodimer-2 (EthD-2), POPO-1, POPO-3, BO-PRO-1, YO-PRO-1 and TO-PRO-1, among which propidium iodide is preferred. These nucleotide fluorescent dyes preferably have a fluorescent spectrum different from the fluorescent labeling compound for the fluorescent labeled antibody which binds specifically with leukocytes in step (i), as described above.

End concentration of the nucleotide fluorescent dye is about 0.003 mg/L to 200 mg/L, preferably about 0.03 mg/L to 70 mg/L, more preferably about 0.3 mg/L to 35 mg/L. The end concentration here means a concentration in a mixture of the hematologic sample, the fluorescent labeled antibody and the nucleotide fluorescent dye which is subjected to flowcytometry, or in the case where another agent is used as described below, in a mixture just about to be subjected to flowcytometry, preferably.

In order to raise the permeability only of the erythroblasts to the above-mentioned nucleotide fluorescent dye, for example, ① a first reagent fluid of hypotonic osmolarity containing a buffer for maintaining pH within an acidic range is admixed to the hematologic sample, and ② admixed thereto is a second reagent fluid containing a buffer for neutralizing the mixture of the hematologic sample and the first reagent fluid in step ① and adjusting the pH of the mixture to a level suitable for staining and an osmolarity compensating agent for adjusting the osmolarity of the mixture within such a range as retains the shape and integrity of leukocytes.

The first reagent fluid in step ① is maintained at a pH within the acidic range, for example, from about 2.0 to 5.0, preferably from about 2.5 to 4.0, and more preferably from about 3.0 to 3.5, for effective lysis of erythrocytes. If the pH is too low, the reagent fluid does excessive damage to not only erythrocytes but also leukocytes, erythroblasts and the fluorescent labeled antibody specific to leukocytes. If the pH is too high, the action of the reagent fluid lysing erythrocytes is restrained.

The buffer to maintain the pH within the above-mentioned range is a buffer having an acid dissociation constant pKa of about 3.0±2.0. Examples of such buffers are malic acid and its salt, succinic acid and its salt, citric acid and its salt, phosphoric acid and its salt, and Good's buffer. The concentration of the buffer is not particularly limited so long as it is enough for maintaining the pH of the first reagent fluid at about 2.0 to 5.0. For example, the concentration may be 5 to 50 mM/l.

The first reagent fluid is required to have a hypotonic osmolarity, for example, an osmotic pressure not exceeding about 100 mOsm/kg·$H_2O$, more preferably from about 10 to 60 mOsm/kg·$H_2O$. The kind of osmolarity compensating agent for adjusting the first reagent fluid within the above range of osmotic pressure is not particularly limited, but examples thereof are alkali metal salts and saccharides. For example, sodium chloride or sucrose may be used in a concentration of about 0.1 g/L to 2.0 g/L, for example. However, in the case where the first reagent fluid can compensate the above osmotic pressure by itself, it may not be necessary to use the osmolarity compensating agent.

The hematologic sample is treated with the first reagent fluid for a time period necessary for complete lysis of erythrocytes, for example, for about 5 to 120 seconds, preferably for about 10 to 60 seconds, more preferably for about 20 to 40 seconds.

The mixture ratio of the hematologic sample to the first reagent fluid is not particularly limited. However, in consideration of operation by a flowcytometer, the mixture ratio may be about 1:5 to 1:200 by volume, for example.

The second reagent fluid in step ② contains the buffer to neutralize the mixture of the hematologic sample and the first reagent fluid and adjust the mixture to a pH suitable for staining and the osmolarity compensating agent to adjust the mixture to an osmotic pressure suitable for retaining the shape and integrity of leukocytes.

The pH of the second reagent fluid which neutralizes acidity of the first reagent fluid and is suitable for staining is, for example, about pH 5.0 to pH 11.0, preferably about pH 7.5 to pH 10.0. The kind of a buffer used for maintaining the pH within these ranges is not particularly limited, but a buffer having a pKa of about 9.0±2.0 is preferred. Examples thereof are phosphoric acid and its salt, HEPES, Tricine, and the like. The concentration of the buffer is not particularly limited so far as it can maintain the second reagent fluid at a pH about 5.0 to 11.0, for example, 5 to 100 mM/l.

The osmotic pressure of the second reagent fluid suitable for retaining the shape and integrity of leukocytes is about 300 mOsm/kg·$H_2O$ to 1000 mOsm/kg·$H_2O$, more preferably 400 mOsm/Kg·$H_2O$ to 600 mOsm/kg·$H_2O$. The kind of an osmolarity compensating agent used for adjusting the osmotic pressure within the above ranges is not particularly limited. Examples thereof are alkali metal salts and saccharides. For example, sodium chloride or sucrose may be used in a concentration of about 10.0 g/L to 20.0 g/L, for example.

The mixture ratio of the first reagent fluid to the second reagent fluid can be suitably adjusted depending on the pH and amount of the first reagent fluid used formerly, the concentration of the osmolarity compensating agent in the first reagent fluid, and the pH of the second reagent fluid, the concentration of the osmolarity compensating agent in the second reagent fluid and the like. For example, in the case where the pH and the osmotic pressure of the first reagent fluid are 3.0 and 16 mOsm/kg·$H_2O$, respectively, and the pH and the osmotic pressure of the second reagent fluid are 7.5 and 400 mOsm/kg·$H_2O$, respectively, the mixture ratio of the first reagent fluid to the second reagent fluid is preferably about 1:1 to 1:5.

For retaining the shape and integrity of leukocytes in the hematologic sample in step (ii) of the present invention, the osmotic pressure after the addition of the first reagent fluid and the second reagent fluid is preferably within the range from about 100 to 500 mOsm/kg·$H_2O$, more preferably from 200 to 400 mOsm/kg·$H_2O$. If the osmotic pressure after the addition of the first reagent fluid and the second reagent fluid is out of this range, it is preferable that the second reagent fluid contains an osmolarity compensating agent. The kind of the osmolarity compensating agent is not particularly limited, but is preferably a substance capable of maintaining normal biological cells at physiologic osmotic pressure, such as an alkali metal or a saccharide.

In step (iii) of the present invention, the nuclei of the erythroblasts are stained. For staining the nuclei of the erythroblasts, the hematologic sample treated in the above-described steps is stained with the nucleotide fluorescent dye. More particularly, the nucleotide fluorescent dye may be added to the first reagent fluid or second reagent fluid beforehand, and this first reagent fluid or second reagent fluid containing the nucleotide fluorescent dye may be mixed with the hematologic sample. Alternatively, a reagent fluid containing the nucleotide fluorescent dye may be separately added. The timing of adding the reagent fluid containing the nucleotide fluorescent dye is not limited, but it is preferred that the nucleotide dye is added into the first reagent fluid beforehand. A time required for the staining of the nuclei of the erythroblasts is about 1 to 120 minutes, preferably in about 3 to 30 minutes, more preferably in about 5 to 10 minutes, after the hematologic sample is mixed with all the reagents.

The flowcytometer used in step (iv) of the present invention is not particularly limited, and may be a commercially available one. By use of such a flowcytometer, at least two fluorescent signals are detected for each cell. The fluorescent signals to be detected depend on what kind of fluorescent labeling compound is used for the fluorescent labeled antibody and what kind of nucleotide fluorescent dye is used. The fluorescent signals may be of a combination of red and green fluorescence, a combination of red and orange fluorescence, and a combination of green and orange fluorescence, among which the combination of red and green fluorescence is preferred.

In step (v) of the present invention, erythroblasts are discriminated and counted based on difference in intensity between the above-mentioned at least two fluorescent signals. For example, in the case where two fluorescent signals are detected, a two-dimensional distribution chart (scattergram) is preferably produced by plotting the fluorescence based on the fluorescent labeled antibody which binds specifically with leukocytes and the fluorescence based on the nucleotide fluorescent dye in two axes. An area in which erythroblasts appear may be defined on this two-dimensional distribution chart. The erythroblast count can be obtained by counting the number of cells in this area. An area in which leukocytes appear as well as the area in which erythroblasts appear may be defined on this two-dimensional distribution chart. The number of cells is counted in the individual areas to obtain the erythroblast count and leukocyte count. The erythroblast count is divided by the leukocyte count and thereby the ratio of erythroblasts to leukocytes can be obtained. Alternatively a ratio between erythroblasts and total number of nucleated cell, i.e., erythroblast and leukocyte count combined, may be obtained.

Figure 6:
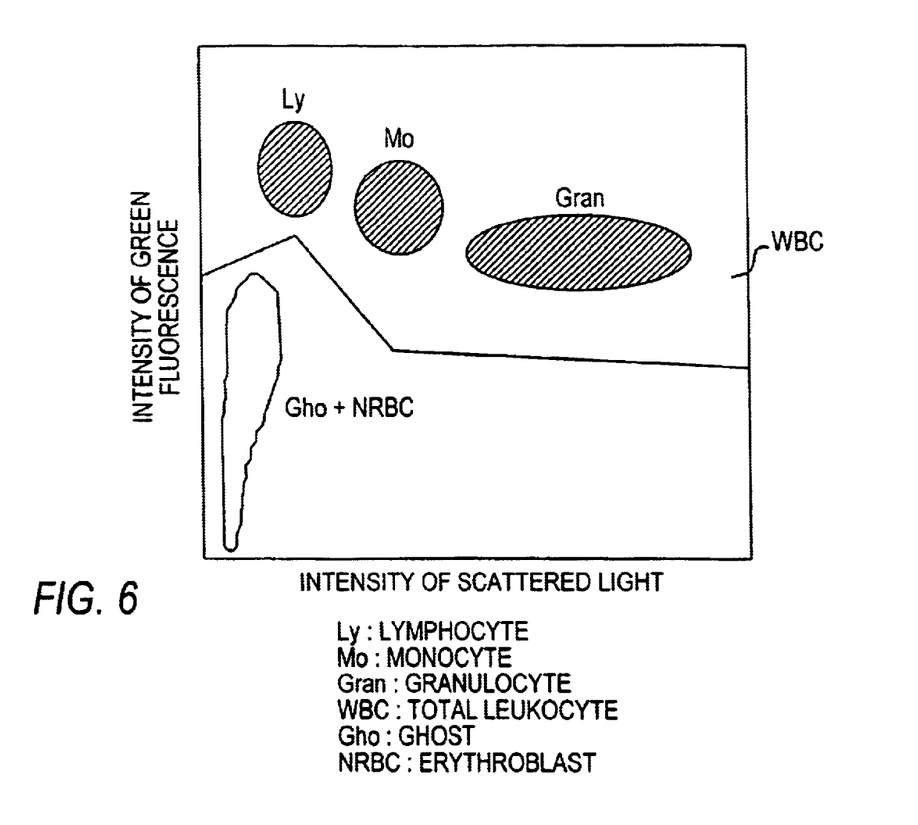
FIG. 6 is a scattergram in the case where scattered light signals are combined with the method for discriminating and counting erythroblasts in accordance with the present invention.

Additionally, in the case where membranes of leukocytes are excessively damaged by effect of added agents and leukocytes cannot be clearly distinguished from erythroblasts in the two-dimensional distribution chart on which the nucleotide fluorescence (red fluorescence in the examples) and the fluorescence based on the fluorescent labeled antibody (green fluorescence in the examples) are plotted in the two axes, the following two steps may further be added in step (iv) for the purpose of discriminating and counting erythroblasts more accurately:

(a) Scattered light signals are also detected, and the scattered light (e.g., side scattered light signals, forward scattered light and the like, preferably side scattered light) and the fluorescence based on the fluorescent labeled antibody are plotted on two axes to produce a two-dimensional distribution chart. From this distribution chart, the group of leukocytes is identified. (see FIG. 6.)

(b) In a distribution chart on which the nucleotide fluorescence and the fluorescence based on the fluorescent labeled antibody are plotted in the two axes, an area in which the corresponding group of leukocytes is distributed is defined. (see FIG. 7.)

Figure 7:
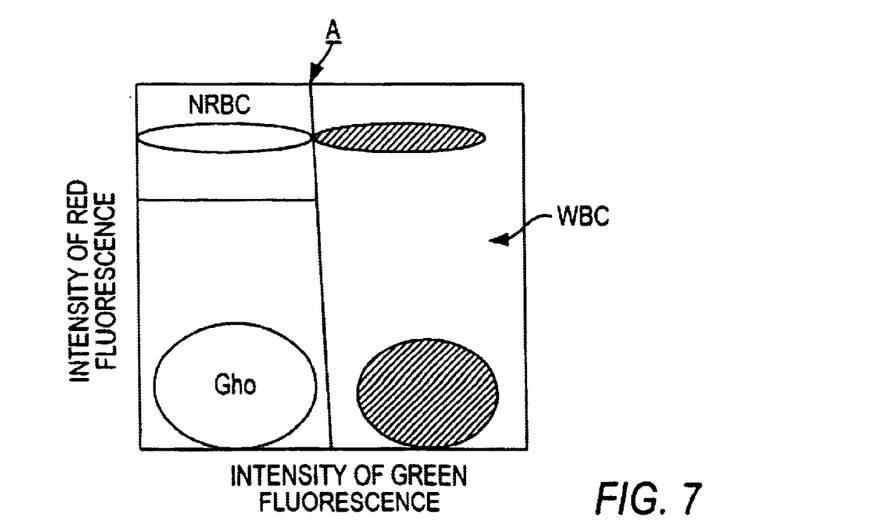
FIG. 7 is a scattergram in which erythroblasts are distinguished from ghosts in a group of ghosts and nucleated red blood cells in FIG. 6.

(c) A boundary A between the group of leukocytes and a group of erythroblasts is marked in the two-dimensional distribution chart of (b).

Further, in the case where the end concentration of the nucleotide fluorescent dye is 0.003 mg/L to 10 mg/L in step (ii), the population of erythroblasts can be classified into at least two groups according to the degree of maturity of the erythroblasts which is judged from difference basis of intensity of fluorescent light caused by the nucleotide fluorescent dye. More preferably, a suitable end concentration of the nucleotide fluorescent dye is 0.03 mg/L to 3 mg/L.

In this case, in step (v), it is possible to measure the maturation and count erythroblasts in different maturation stages from difference in intensity of fluorescence based on the nucleotide fluorescent dye, in other words, it is possible to determine an area where erythroblasts are present in the scattergram; determine sub-areas of groups of erythroblasts in different stages of maturity in the determined erythroblast area from difference in intensity of fluorescent light caused by the nucleotide fluorescent dye; count the number of cells in each of the sub-areas; divide the number of erythroblasts in each of the stages of maturity by the number of all the erythroblasts to obtain a ratio of erythroblasts in each of the stages of maturity to the whole erythroblasts.

The classification of erythroblasts according to their degrees of maturity means classifying morphologic pro-erythroblast basophilic erythroblasts, polychromatophilic erythroblasts, orthochromatic erythroblast or the like in erythroblasts into at least two groups or into the respective groups. For example, erythroblasts are classified into pro-erythroblasts and three groups of basophilic erythroblasts, polychromatophilic erythroblasts and orthochromatic erythroblasts, in Example 3.

EXAMPLE

Examples of the method for discriminating and counting erythroblasts are now described.

Example 1

First, reagents having the following compositions were prepared.

Fluorescent Labeled Antibody:
 FITC labeled anti-CD45 antibody
First Reagent Fluid (pH 3.0, Osmotic Pressure 16 mOsm/kg·H$_2$O):
 Buffering agent—Citric acid monohydrate, 2.10 g/l
  —Disodium hydrogenphosphate, 0.56 g/l
 Nucleotide fluorescent dye
  —Propidium iodide, 100 mg/l
 Purified water
Second Reagent Fluid (pH 7.5, Osmotic Pressure 420 mOsm/kg·H$_2$O):
 Buffering agent—Sodium dihydrogenphosphate dihydrate, 0.95 g/l
  Disodium hydrogenphosphate, 6.24 g/l
 Osmolarity compensating agent
  —Sodium chloride, 10.2 g/l
 Purified water Fifty (50) μl of blood from a patient was added to peripheral blood to produce a hematologic sample. These bloods had been treated with an anticoagulant. Ten (10) μl of the above FITC labeled anti-CD45 antibody were added to the hematologic sample. This mixture was incubated at room temperature for about 15 minutes. Here, the blood containing erythroblasts and the peripheral blood were used within eight hours after they were collected.

Then, 500 μl of the first reagent fluid were added to the mixture, which was incubated at room temperature for about 30 seconds. To the resulting mixture, 1000 μl of the second reagent fluid were added and then the mixture was incubated at room temperature for about 5 minutes. Then, fluorescences of wavelengths of 530 nm (green) and 650 nm (red) were detected for individual cells contained in the obtained hematologic sample by a flowcytometer equipped with an argon ion laser of 488 nm wavelength as a light source.

Figure 1:
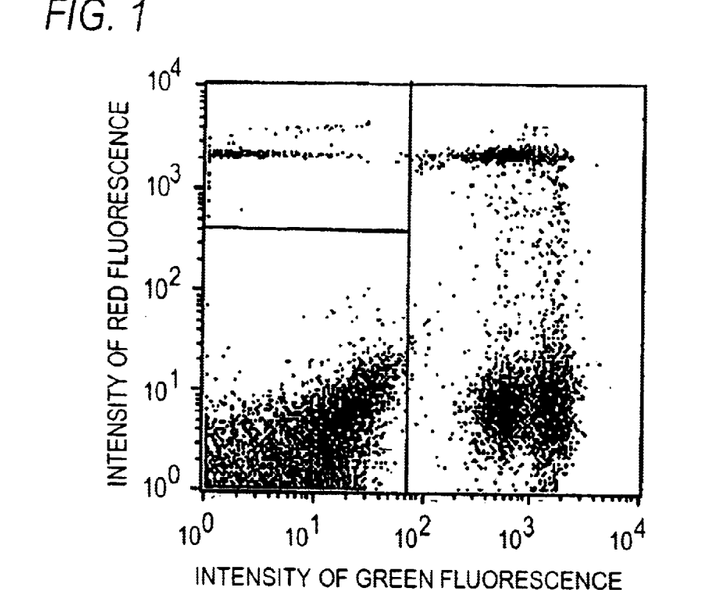
FIG. 1 is a scattergram obtained by the method for discriminating and counting erythroblasts in accordance with the present invention.

FIG. 1 is a scattergram showing distribution of the cells in which the intensity of green fluorescence and that of red fluorescence are plotted in coordinate axes.

In FIG. 1, there were observed four groups: leukocytes, red fluorescent-stained leukocytes, erythroblasts and ghosts.

Figure 2:
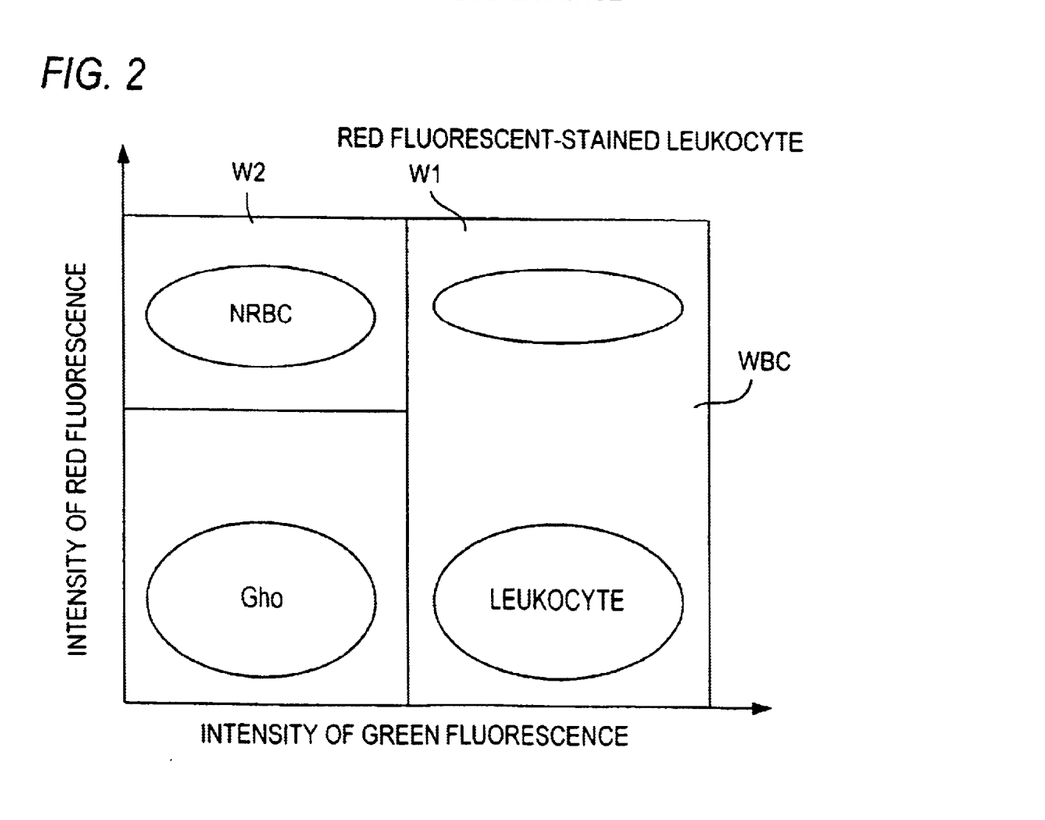
FIG. 2 is a schematic view of FIG. 1.

Analysis was made as follows: First the leukocytes and red fluorescent-stained leukocytes were enclosed in a window (W1) as shown in FIG. 2, and all counted to obtain the leukocyte count. Next, all erythroblasts were enclosed by another window (W2) and were counted to obtain the erythroblast count. The obtained erythroblast count was divided by the obtained leukocyte count to obtain the ratio of the erythroblasts to the leukocytes.

Separately from the above example, the same hematologic sample as in Example 1 was subjected to a manual microscopic method (May Grünwald-Giemsa stain, 1,000

WBC count) discrimination and counting to obtain the morphologic erythroblast count.

Figure 3:
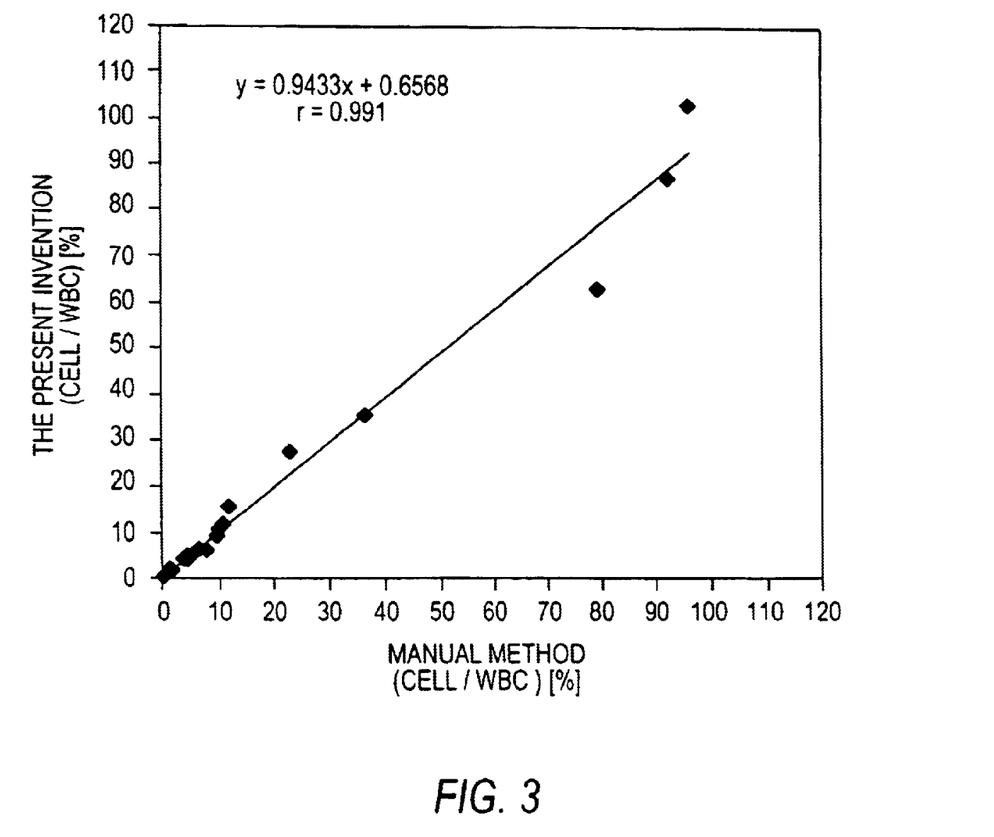
FIG. 3 is a graph showing correlation between the ratio of erythroblasts to leukocytes counted by the method of the present invention and that counted by a manual microscopic method.
Figure 4A:
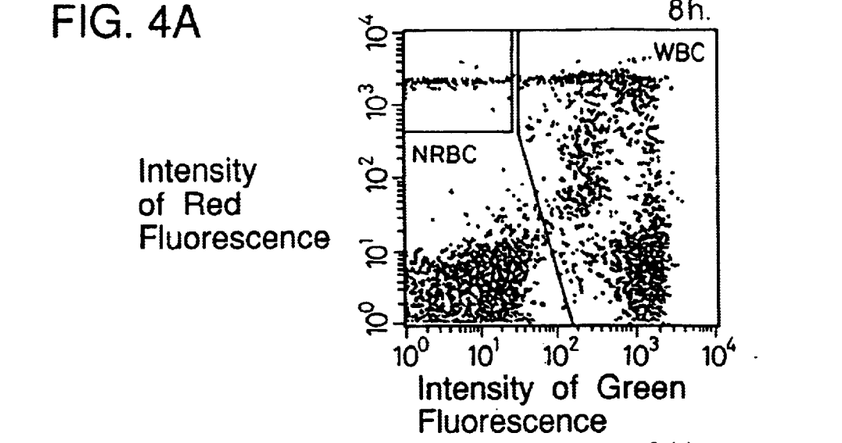
FIGS. 4A to 4C show changes with time in scattergrams obtained by the method for discriminating and counting erythroblasts in accordance with the present invention.
Figure 4B:
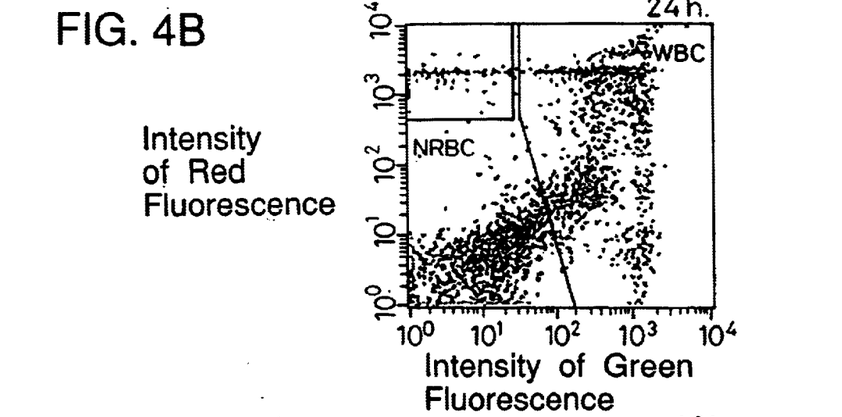
Figure 4C:
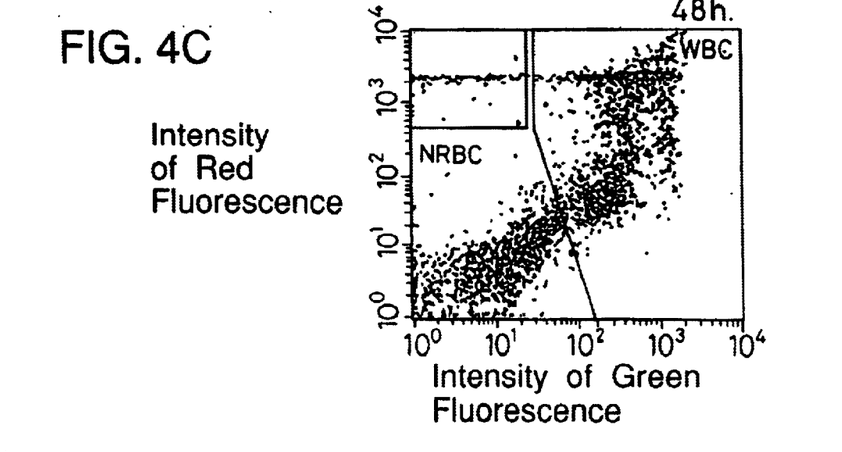
Figure 5A:
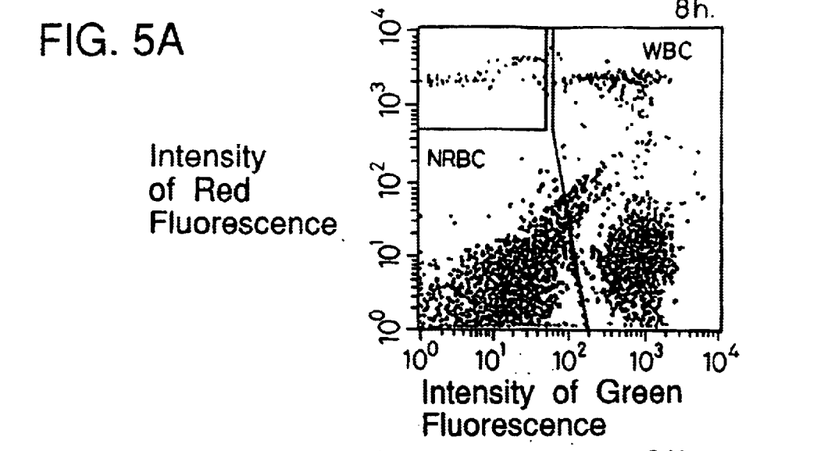
FIGS. 5A to 5C show changes with time in scattergrams in another sample obtained by the method for discriminating and counting erythroblasts in accordance with the present invention.
Figure 5B:
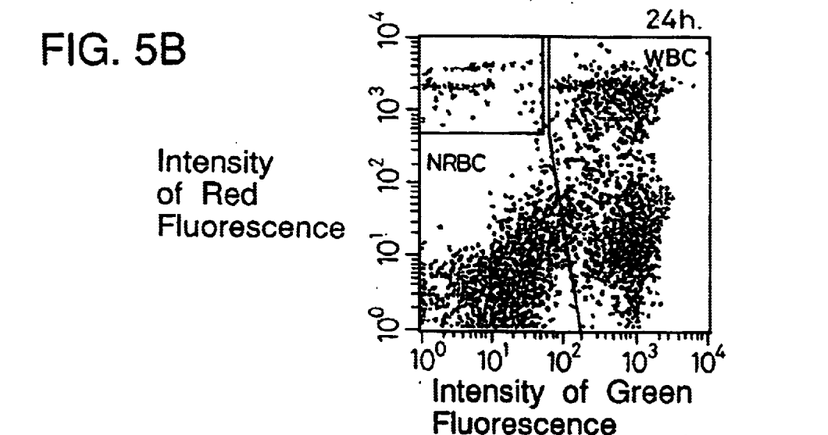
Figure 5C:
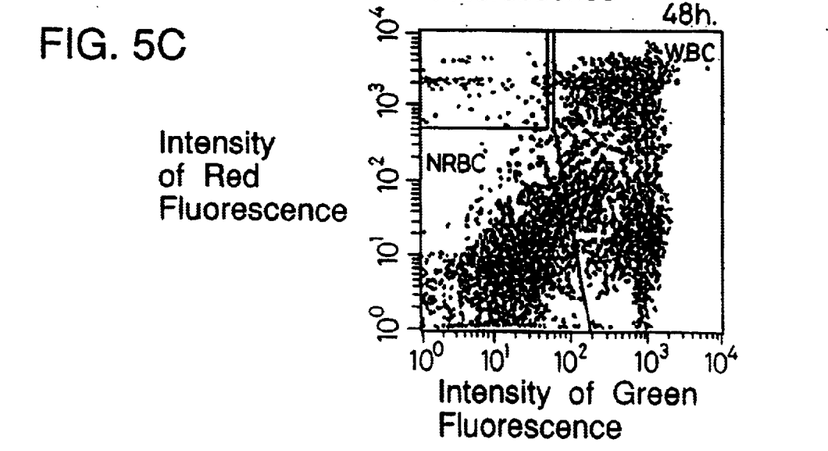

FIG. 3 shows a correlation between the ratio of erythroblast determined by the flowcytometer in accordance with the present invention and that determined by the manual microscopic method.

From FIG. 3, correlation coefficient r is 0.991, which shows that the method of the present invention is remarkably accurate in discriminating and counting erythroblasts.

Example 2

Blood containing erythroblasts from two patients other than the patient in Example 1 and peripheral blood (preserved at room temperature for 8 hours, 24 hours, 48 hours after collection) were examined about leukocytes and erythroblasts in the same manner as in Example 1. The results are shown in FIGS. 4A to 4C and FIGS. 5A to 5C.

The ratio of the erythroblasts to the leukocytes was also calculated for each of the samples. The results are shown in Table 1.

TABLE 1

|  | after 8 hours | after 24 hours | after 48 hours |
|---|---|---|---|
| Sample 1 | 3.6% | 3.6% | 3.6% |
| Sample 2 | 6.1% | 6.1% | 6.7% |

FIGS. 4A to 4C and 5A to 5C and Table 1 show that the passing of time hardly affects the results of examination according to the present invention.

Example 3

Reagents having the following compositions were prepared.
Fluorescent Labeled Antibody:
  FITC labeled anti-CD45 antibody
First Reagent Fluid (pH 3.0, Osmotic Pressure 16 mOsm/kg):
  Buffering agent—Citric acid monohydrate, 2.10 g/l
    —Disodium hydrogenphosphate, 0.56 g/l
  Nucleotide fluorescent dye
    —Propidium iodide, 1 mg/l
  Purified water
Second Reagent Fluid (pH 7.5, Osmotic Pressure 420 mOsm/kg):
  Buffering agent—Sodium dihydrogenphosphate dihydrate, 0.95 g/l
    Disodium hydrogenphosphate, 6.24 g/l
  Osmolarity compensating agent
    —Sodium chloride, 10.2 g/l
  Purified water Fifty (50) μl of blood from a patient was mixed with ten (10) μl of the above FITC labeled anti-CD45 antibody. These bloods had been treated with an anticoagulant. This mixture was incubated at room temperature for about 15 minutes.

Then, 500 μl of the first reagent fluid were added to the mixture, which was incubated at room temperature for about 30 seconds. To the resulting mixture, 1000 μl of the second reagent fluid were added and then the mixture was incubated at room temperature for about 5 minutes. Then, fluorescences of wavelengths of 530 nm (green) and 650 nm (red) were detected about individual cells contained in the obtained hematologic sample by a flowcytometer equipped with an argon ion laser of 488 nm wavelength as a light source.

Figure 8:
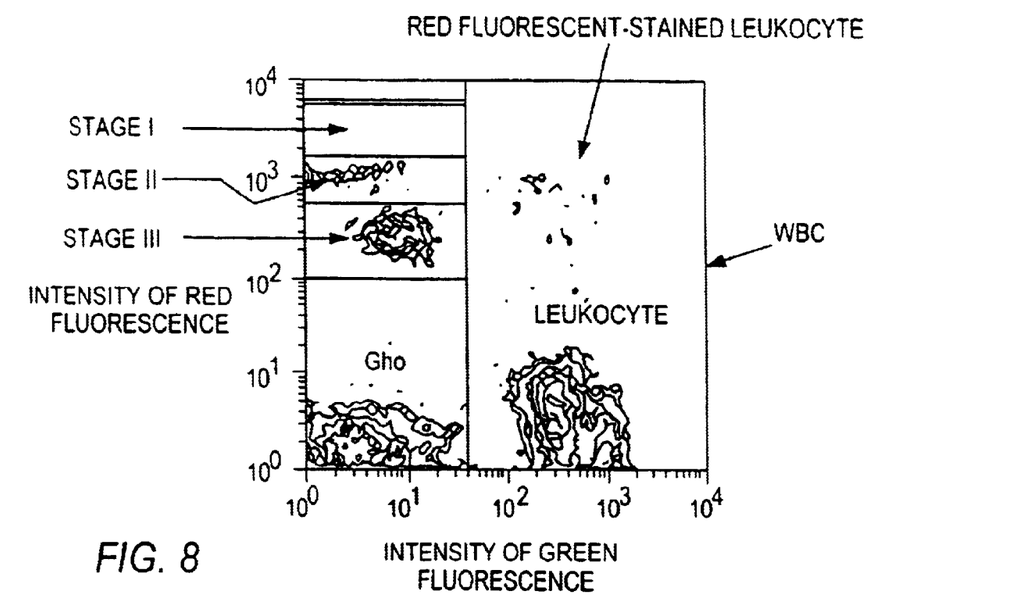
FIG. 8 is a scattergram showing distribution of individual cells with intensity of green fluorescence and that of red fluorescence as coordinate axes used for NRBC staging.

FIG. 8 is a scattergram showing distribution of the cells in which the intensity of green fluorescence and that of red fluorescence are plotted in coordinate axes.

In FIG. 8, there were observed six groups: leukocytes, red fluorescent-stained leukocytes, mature erythroblasts, immature erythroblasts 1, immature erythroblasts 2 and ghosts.

Figure 9:
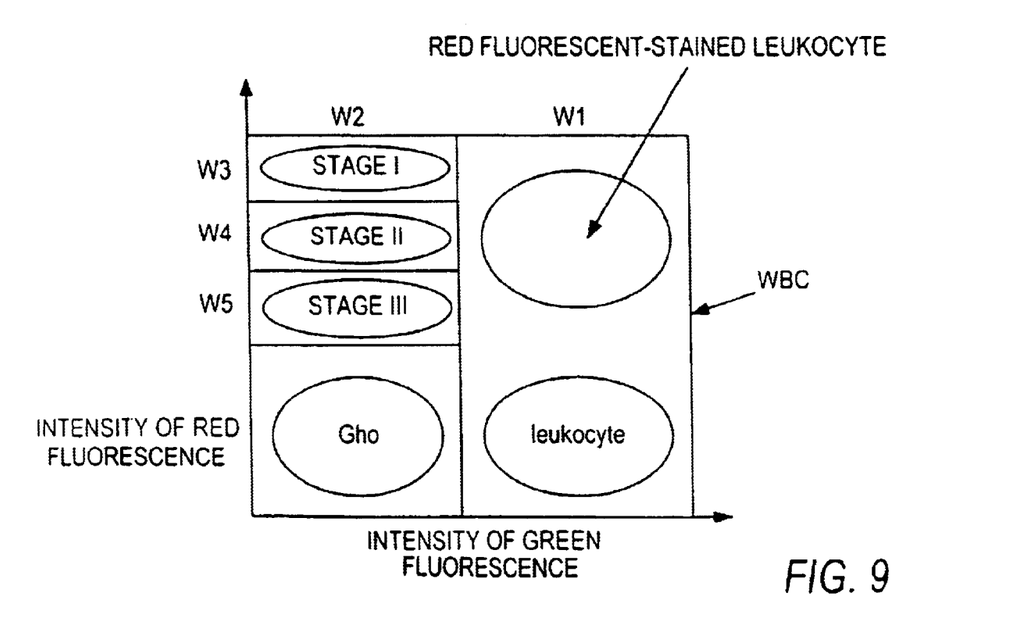
FIG. 9 illustrates enclosure of each group of blood cells with windows for analysis.

Analysis was made as follows: First the leukocytes and red fluorescent-stained leukocytes were enclosed in a window (W1) as shown in FIG. 9, and all counted to obtain the leukocyte count. Next, all erythroblasts were enclosed by another window (W2) and were counted to obtain the total erythroblast count. Then Stage I, Stage II and Stage III in the window (W2) were enclosed by windows (W3), (W4) and (W5), respectively. The erythroblasts in the respective windows were counted to obtain the erythroblast staging count. The erythroblast number in the individual window was divided by the total erythroblast number to obtain the proportion of erythroblast in different stages.

Separately from the above example, the same hematologic sample as in Example 3 was subjected to a manual microscopic method (May Grünwald-Giemsa stain) discrimination and counting to classify morphologically erythroblasts into proerythroblasts, balophilic erythroblasts, polychromatophilic erythroblasts and orthochromatic erythroblasts and count the numbers thereof.

Table 2 shows results determined by the flowcytometer in accordance with the present invention and results determined by the manual microscopic method.

TABLE 2

| | Method of the Invention | | Manual Microscopic Method | |
|---|---|---|---|---|
| Stage I | 0.7% | Proerythroblast plus Basophilic erythroblast | 0% |
| Stage II | 17.6% | Polychromatophilic Erythroblasts | 18% |
| Stage III | 81.7% | Orthochromatic Erythroblast | 82.0% |

Table 2 shows that the results by the method the present invention agrees well with the results by the manual microscopic method.

Example 4

Figure 10:
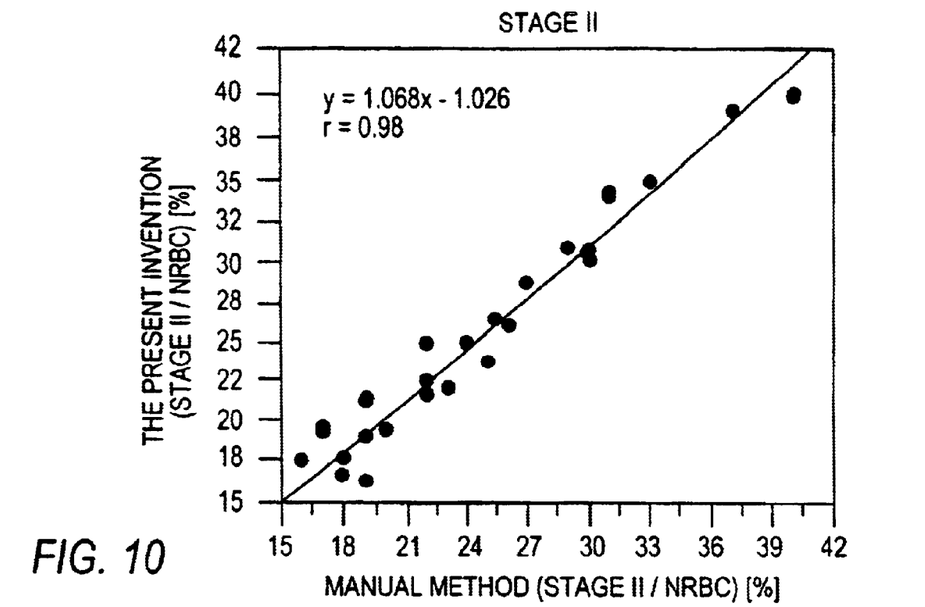
FIG. 10 is a graph showing correlation between the ratio of Stage II to total erythroblast counted by the method of the present invention and that counted by a manual microscopic method.
Figure 11:
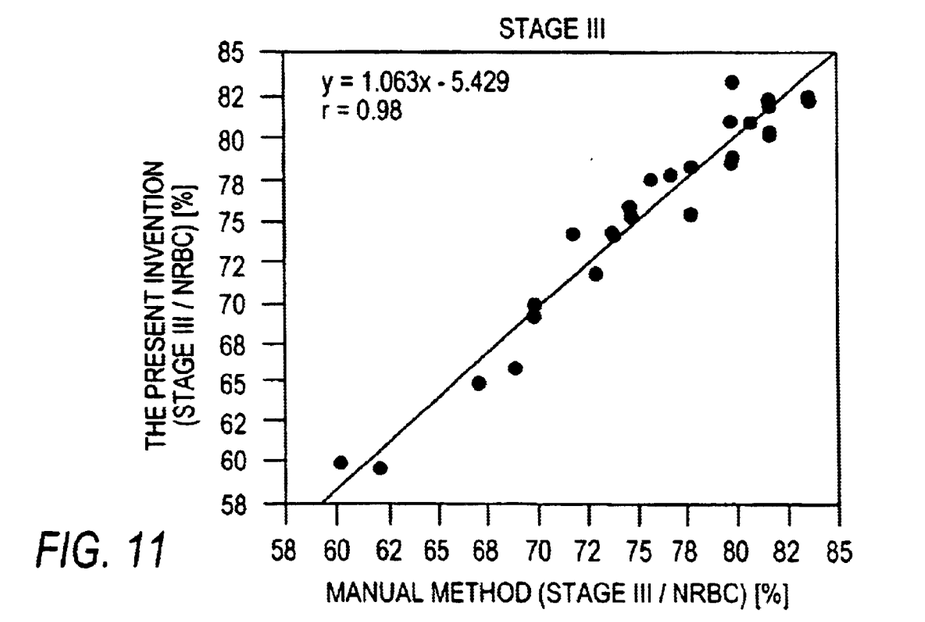
FIG. 11 is a graph showing correlation between the ratio of State III to total erythroblast counted by the method of the present invention and that counted by a manual microscopic method.

Twenty-four (24) samples of bloods form patients were determined by the method of the above Example 3. Correlation between the method of the invention and the manual microscopic method was analyzed. Results were shown in FIGS. 10 and 11. FIGS. 10 and 11 shown that the method of the invention has a definite correlation with the manual microscopic method and is capable of classifying and counting erythroblasts in the different maturity stages with great accuracy.

What is claimed is:
1. A method for discrimination and counting erythroblasts comprising the steps of:
  (i) staining leukocytes in a hematologic sample by adding a fluorescent leukocyte binding antibody to the hematologic sample to bind the leukocytes;
  (ii) raising the permeability only of cell membranes of erythroblasts in the hematologic sample to a nucleotide fluorescent dye which does not permeate a cell membrane when the permeability is not raised, the nucleotide fluorescent dye having a fluorescent spectrum that is distinguishable from that of a fluorescent labeling compound of the fluorescent labeled antibody in step (i);

(iii) staining nuclei of the erythroblasts in the hematologic sample with the nucleotide fluorescent dye;

(iv) analyzing the hematologic sample using flow cytometry to detect the nucleotide fluorescent signal of the stained erythroblasts and the fluorescent signal of the labeled antibody bound to the leukocytes; and (v) plotting the nucleotide fluorescent signal and the fluorescent labeled antibody signal in two coordinate axes to obtain a two-dimensional distribution chart discriminating between erythroblasts and leukocytes in the hematologic sample based on the difference in the two-dimensional distribution chart and counting the erythroblast.

2. The method according to claim 1, wherein the fluorescent labeled leukocyte binding antibody in the step (i) recognizes an antigen present on the leukocytes surface and binds with the antigen.

3. The method according to claim 1 wherein the fluorescent labeled antibody in the step (i) comprises at least one compound selected from the group consisting of phycoerythrin, fluorescein isothiocyanate, allophycocyanin, Texas Red, arylsulfonate, cyanine fluorescent dye CY5, a peridinin chlorophyll complex and a combination thereof.

4. The method according to claim 1, wherein the raising of the permeability of the cell membranes of erythroblasts in the hematologic sample to the nucleotide fluorescent dye in step (ii) comprises the steps of:

(i) admixing a first reagent fluid of hypotonic osmolarity containing a buffer for maintaining pH within an acidic range to the hematologic sample after the step (i); and (ii) admixing thereto a second reagent fluid containing a buffer for maintaining a pH from 5.0 to 11.0 and an osmolarity compensating agent for adjusting an osmolarity from 300 to 1000 mOsm/kg $H_2O$.

5. The method according to claim 1, wherein the staining of the nuclei of the erythroblasts in the step (iii) is carried out by mixing the hematologic sample with the nucleotide fluorescent dye.

6. The method of claim 5, wherein the nucleotide fluorescent dye comprises at least one compound selected from the group consisting of propidium iodide, N-methyl-4-(1-pyrene)-vinyl-propidium iodide, ethidium bromide, TOTO-1, TOTO-3, YOYO-1, YOYO-3, BOBO-1, BOBO-3, ethidium homodimer-1, ethidium homodimer-2, POPO-1, POPO-3, BO-PRO-1, YO-PRO-1 and TO-PRO-1.

7. The method according to claim 1, wherein the nucleotide fluorescent signal of the erythroblasts and the fluorescent labeled antibody signal of the leukocyte are plotted in two coordinate axes to obtain a two-dimensional distribution chart.

8. The method according to claim 1, wherein an area in which the erythroblasts appear is defined on the two dimensional distribution chart and the number of erythroblast cells in the area is counted.

9. The method according to claim 1, wherein areas in which the leukocytes and the erythroblasts appear are defined on the two-dimensional distribution chart, the number of cells in each of the areas is counted to obtain a leukocyte count and an erythroblast count, and the erythroblast count is divided by the leukocyte count, whereby the ratio of erythroblasts to leukocytes is obtained.

10. The method according to claim 5, wherein the nucleotide fluoresecent dye is used at a concentration within the range of 0.003 mg/L to 10 mg/L to form a mixture to be analyzed using flow cytometry to stain erythroblasts whereby the erythroblasts are classified into at least two groups according to the degrees of maturity thereof.

11. The method according to claim 10, wherein:

(i) the nucleotide fluorescent signal of the erythroblasts and the fluorescent labeled antibody signal of the leukocytes are plotted in two coordinate axes to obtain a two-dimensional distribution chart;

(ii) areas are set in the two-dimensional distribution chart for classifying erythroblasts into at least two groups from difference in intensity of the fluorescent signals based on the nucleotide fluorescent dye; and (iii) the number of cells in each of the areas is counted for obtaining counts of erythroblasts at different degrees of maturity.

12. The method of according to claim 11, wherein an area of all erythroblasts and areas of at least two groups of erythroblasts at different degrees of maturity are defined in the two-dimensional distribution chart, the number of cells in each of the areas is counted to obtain a total erytbroblast count and counts of erythroblasts at the respective degrees of maturity, and the counts of erythroblast at the respective degrees of maturity are divided by the total erythroblast count, whereby the ratios of the erythroblasts at the respective degrees of maturity to all the erythroblasts are obtained.

13. The method according to claim 4 wherein the osmolarity of the mixture is from about 400 mOsm/Kg.$H_2O$ to about 600 mOsm/Kg.$H_2O$.

* * * * *